(12) United States Patent
Bhatnagar et al.

(10) Patent No.: US 7,888,490 B2
(45) Date of Patent: Feb. 15, 2011

(54) PROCESS FOR THE PREPARATION OF NON-TOXIC ANTHRAX VACCINE

(75) Inventors: Rakesh Bhatnagar, New Delhi (IN); Pankaj Gupta, New Delhi (IN); Smriti Batra, New Delhi (IN); Vibha Chauhan, New Delhi (IN); Aparna Singh, New Delhi (IN); Nidhi Ahuja, New Delhi (IN); Praveen Kumar, New Delhi (IN)

(73) Assignee: Centre of Biotechnology Jawaharlal Nehru University, New Delhi (IN)

( * ) Notice: Subject to any disclaimer, the term of this patent is extended or adjusted under 35 U.S.C. 154(b) by 0 days.

(21) Appl. No.: 10/497,673

(22) PCT Filed: Mar. 20, 2002

(86) PCT No.: PCT/IN02/00048
§ 371 (c)(1),
(2), (4) Date: Nov. 3, 2004

(87) PCT Pub. No.: WO03/048390
PCT Pub. Date: Jun. 12, 2003

(65) Prior Publication Data
US 2005/0063986 A1  Mar. 24, 2005

(30) Foreign Application Priority Data
Dec. 5, 2001 (IN) .............................. 1222/DEL/01

(51) Int. Cl.
*C07H 21/04* (2006.01)
*C07H 21/02* (2006.01)
*A61K 39/07* (2006.01)

(52) U.S. Cl. ...................... 536/23.7; 536/23.1; 424/9.1; 424/9.2; 424/184.1; 424/234.1; 424/246.1; 424/93.1; 424/93.2; 435/41; 435/69.1; 435/71.1; 435/440; 530/300; 530/350

(58) Field of Classification Search .................. 424/9.1, 424/9.2, 184.1, 234.1, 246.1, 93.1, 93.2; 435/41, 69.1, 71.1, 440, 471, 320.1; 530/300, 530/350; 536/23.1, 23.7
See application file for complete search history.

(56) References Cited
FOREIGN PATENT DOCUMENTS
WO    01/82788 A2   11/2001

OTHER PUBLICATIONS

Kumar, P., et al Infection and Immunity, vol. 69, No. 10, pp. 6532-6536, Oct. 2001.*

P. Gupta, et al, "Enhanced Expression of the Recombinant Lethal Factor of *Bacillus anthracis* by Fed-Batch Culture" *Biochemical and Biophysical Research Communications*, (2001) vol. 285 p. 1025-1033.

V. Chauhan, et al "Constitutive Expression of Protective Antigen Gene of *Bacillus anthracis* in *Escherichia coli*" *Biochemical and Biophysical Research Communications*, (2001) vol. 283 p. 308-315.

P. Gupta, et al "Expression and Purification of the Recombinant Protective Antigen of *Bacillus anthracis*" *Protein Expression and Purification* (1999) vol. 16 p. 369-376.

B.R. Sellman, et al "Point Mutations in Anthrax Protective Antigen That Block Translocation" *The Journal of Biological Chemistry* (2001) vol. 276 p. 8371-8376.

S. Batra, et al "Trp 346 and Leu 352 Residues in Protective Antigen Are Required for the Expression of Anthrax Lethal Toxin Activity" *Biochemical and Biophysical Research Communications* (2001) vol. 281 p. 186-192.

N. Ahuja, et al Hydrophobic Residues Phe552, Phe554, Ile562, Leu566, and Ile574 Are Required for Oligomerization of Anthrax Protective Antigen *Biochemical and Biophysical Research Communications* (2001) vol. 287 p. 542-549.

J. Mogridge, et al "Involvement of Domain 3 in Oligomerization by the Protective Antigen Moiety of Anthrax Toxin" *Journal of Bacteriology* (200 I) vol. 183 p. 2111-2116.

P. Gupta, et al "Involvement of Residues 147VYYEIGK153 in Binding of Lethal Factor to Protective Antigen of *Bacillus anthracis*" *Biochemical and Biophysical Research Communications*, (2001) vol. 280 p. 158-163.

Y. Singh, et al "A Deleted Variant of *Bacillus anthracis* Protective Antigen Is Non-toxic and Blocks Anthrax Toxin Action in Vivo" *The Journal of Biological Chemistry*, (1989) vol. 264 p. 19103-19107.

* cited by examiner

*Primary Examiner*—Rodney P. Swartz
(74) *Attorney, Agent, or Firm*—Ladas & Parry LLP

(57) ABSTRACT

Anthrax toxin, comprising of protective antigen (PA), lethal factor (LF) and edema factor (EF) is a major virulent factor of *B. anthracis*. Protective antigen, PA is the main component of all the vaccines against anthrax. The protective efficacy of PA is greatly increased if small quantities of LF of EF are incorporated into the vaccines. An ideal vaccine against anthrax should contain PA, LF and EF together, but this combination would be toxic. Therefore, the biologically inactive mutant preparations of PA, LF and EF may be used together for better immunoprotection. The present invention describes the method for generation of recombinant vaccine against anthrax, comprising of non-toxic, mutant anthrax toxin proteins. The procedure involves site-directed mutagenesis of the native genes of the toxin proteins, the expression and purification of the mutant proteins and finally characterization of these proteins.

18 Claims, 2 Drawing Sheets

Figure: 1

*Plasmid map showing:*
- PT5
- lacO
- RBS
- 6XHis
- PA / LF / EF Genes
- 5.7 kb RECOMBINANT PLASMID CONTAINING PA / LF / EF GENES
- Ampr
- ColE1

CLONING OF PA, LF and EF IN pQE30 VECTOR

Figure:2
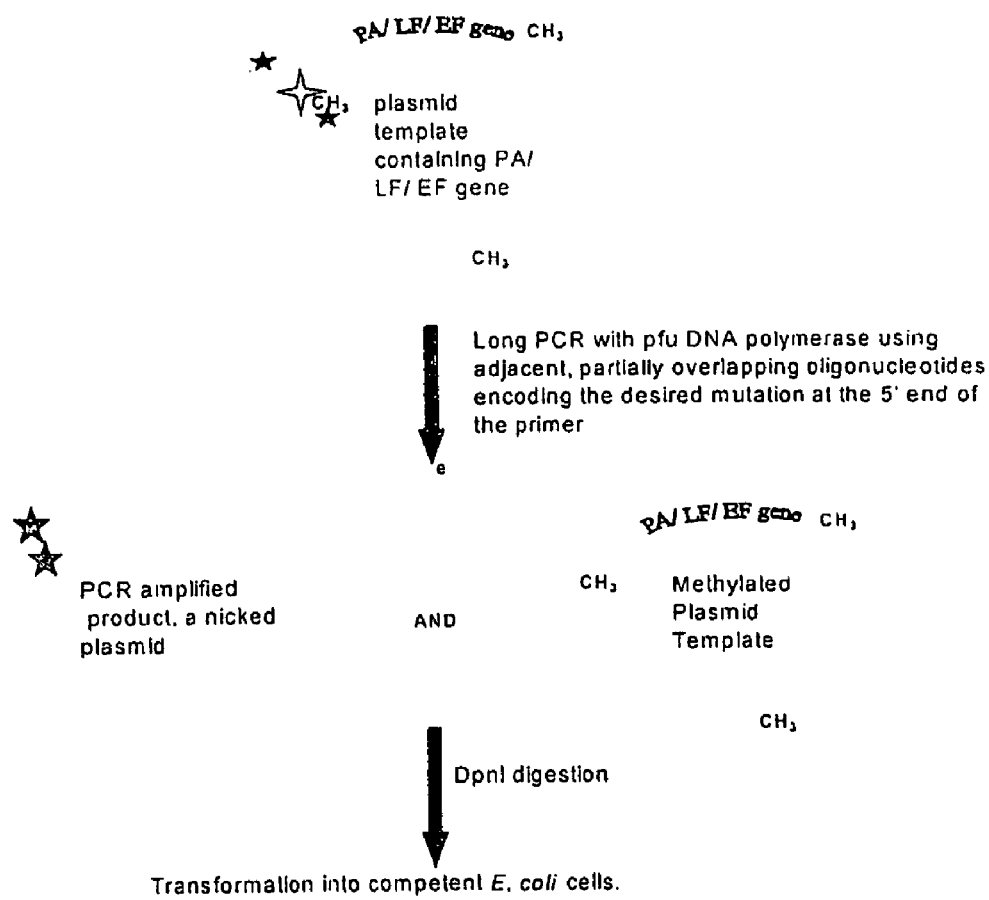
Site-Directed Mutagenesis using long PCR

SEQUENCE LISTING

<160> NUMBER OF SEQ ID NOS: 30

<210> SEQ ID NO 1
<211> LENGTH: 33
<212> TYPE: DNA
<213> ORGANISM: Bacillus anthracis
<220> FEATURE:
<223> OTHER INFORMATION: PA MUTANT: PHE202 RESIDUE CHANGED TO ALANINE

<400> SEQUENCE: 1
cttttcatga atattagaaa tccatgctga aag                                33

<210> SEQ ID NO 2
<211> LENGTH: 39
<212> TYPE: DNA
<213> ORGANISM: Bacillus anthracis
<220> FEATURE:
<223> OTHER INFORMATION: PA MUTANT: LEU203 RESIDUE CHANGED TO ALANINE

<400> SEQUENCE: 2
cttttcatga atattagaaa tccatggtga agcaaaagt                          39

<210> SEQ ID NO 3
<211> LENGTH: 42
<212> TYPE: DNA
<213> ORGANISM: Bacillus anthracis
<220> FEATURE:
<223> OTHER INFORMATION: PA MUTANT: PRO205 RESIDUE CHANGED TO ALANINE

<400> SEQUENCE: 3
cttttcatga atattagaaa tccatggtga aagagcagtt ct                      42

<210> SEQ ID NO 4
<211> LENGTH: 111
<212> TYPE: DNA
<213> ORGANISM: Bacillus anthracis
<220> FEATURE:
<223> OTHER INFORMATION: PA MUTANT: ILE207 RESIDUE CHANGED TO ALANINE

<400> SEQUENCE: 4
tttggttaac cctttctttt catgaatatt agaaatccat ggtgaaagaa aagttctttt   60 attttgaca tcaaccgtat atccttctac ctctaatgaa tcagcgattc c            111

<210> SEQ ID NO 5
<211> LENGTH: 42
<212> TYPE: DNA
<213> ORGANISM: Bacillus anthracis
<220> FEATURE:
<223> OTHER INFORMATION: PA MUTANT:PRO205+TRP226+PHE236 RESIDUES CHANGED
      TO ALANINE

<400> SEQUENCE: 5
cttttcatga atattagaaa tccatggtga aagagcagtt ct                      42

<210> SEQ ID NO 6
<211> LENGTH: 101
<212> TYPE: DNA
<213> ORGANISM: Bacillus anthracis
<220> FEATURE:
<223> OTHER INFORMATION: PA MUTANT:PRO205+TRP226+PHE236 RESIDUES CHANGED
      TO ALANINE

<400> SEQUENCE: 6
ggatttctaa tattcatgaa aagaaaggat taaccaaata taaatcatct cctgaaaaag   60
cgagcacggc ttctgatccg tacagtgatg ccgaaaaggt t                101

<210> SEQ ID NO 7
<211> LENGTH: 40
<212> TYPE: DNA
<213> ORGANISM: Bacillus anthracis
<220> FEATURE:
<223> OTHER INFORMATION: PA MUTANT: PHE552 RESIDUE CHANGED TO ALANINE

<400> SEQUENCE: 7
caagggaaag atatcaccga atttgatgct aatttcgatc                40

<210> SEQ ID NO 8
<211> LENGTH: 28
<212> TYPE: DNA
<213> ORGANISM: Bacillus anthracis
<220> FEATURE:
<223> OTHER INFORMATION: PA MUTANT: ILE574 RESIDUE CHANGED TO ALANINE

<400> SEQUENCE: 8
gaattaaacg cgtctaacgc atatactg                28

<210> SEQ ID NO 9
<211> LENGTH: 39
<212> TYPE: DNA
<213> ORGANISM: Bacillus anthracis
<220> FEATURE:
<223> OTHER INFORMATION: PA MUTANT: PHE552+PHE554 RESIDUES CHANGED TO
      ALANINE

<400> SEQUENCE: 9
attttgagat gtttgttgat cggcattagc atcaaattc                39

<210> SEQ ID NO 10
<211> LENGTH: 58
<212> TYPE: DNA
<213> ORGANISM: Bacillus anthracis
<220> FEATURE:
<223> OTHER INFORMATION: PA MUTANT: ILE562+ILE574 RESIDUES CHANGED TO
      ALANINE

<400> SEQUENCE: 10
cagtatatgc gttagacgcg tttaattccg cttaactgat tcttggcatt ttgagatg                58

<210> SEQ ID NO 11
<211> LENGTH: 39
<212> TYPE: DNA
<213> ORGANISM: Bacillus anthracis
<220> FEATURE:
<223> OTHER INFORMATION: PA MUTANT: LEU566+ILE574 RESIDUES CHANGED TO
      ALANINE

<400> SEQUENCE: 11
atcaggcagc ggaattaaac gcgtctaacg catatactg                39

<210> SEQ ID NO 12
<211> LENGTH: 57
<212> TYPE: DNA
<213> ORGANISM: Bacillus anthracis
<220> FEATURE:
<223> OTHER INFORMATION: PA MUTANT: PHE552+PHE554+ILE562+LEU566+ILE574
      RESIDUES CHANGED TO  ALANINE

<400> SEQUENCE: 12
cagtatatgc gttagacgcg tttaattccg ctgcctgatt cttggcattt tgagatg                57

<210> SEQ ID NO 13
<211> LENGTH: 38
<212> TYPE: DNA
<213> ORGANISM: Bacillus anthracis
<220> FEATURE:
<223> OTHER INFORMATION: PA MUTANT: PHE552+PHE554+ILE562+LEU566+ILE574
      RESIDUES CHANGED TO ALANINE

<400> SEQUENCE: 13
attttgagat gtttgttgat cggcattagc atcaaatt                                38

<210> SEQ ID NO 14
<211> LENGTH: 32
<212> TYPE: DNA
<213> ORGANISM: Bacillus anthracis
<220> FEATURE:
<223> OTHER INFORMATION: PA MUTANT: PHE427 RESIDUE CHANGED TO ALANINE

<400> SEQUENCE: 14
gtaattggag tagaactggc atcgtcttgt gc                                      32

<210> SEQ ID NO 15
<211> LENGTH: 39
<212> TYPE: DNA
<213> ORGANISM: Bacillus anthracis
<220> FEATURE:
<223> OTHER INFORMATION: PA MUTANT: ASP425 RESIDUE CHANGED TO RESIDUE
      DELETED

<400> SEQUENCE: 15
gtaattggag tagaactgaa atcttgttca tttaatgcg                               39

<210> SEQ ID NO 16
<211> LENGTH: 29
<212> TYPE: DNA
<213> ORGANISM: Bacillus anthracis
<220> FEATURE:
<223> OTHER INFORMATION: PA MUTANT: PHE427 RESIDUE CHANGED TO RESIDUE
      DELETED

<400> SEQUENCE: 16
gcacaagacg atagttctac tccaattac                                          29

<210> SEQ ID NO 17
<211> LENGTH: 59
<212> TYPE: DNA
<213> ORGANISM: Bacillus anthracis
<220> FEATURE:
<223> OTHER INFORMATION: PA MUTANT: TRP346 RESIDUE CHANGED TO ALANINE

<400> SEQUENCE: 17
cggtcgcaat tgatcattca ctatctctag caggggaaag aactgcggct gaaacaatg         59

<210> SEQ ID NO 18
<211> LENGTH: 77
<212> TYPE: DNA
<213> ORGANISM: Bacillus anthracis
<220> FEATURE:
<223> OTHER INFORMATION: PA MUTANT: LEU352 RESIDUE CHANGED TO ALANINE

<400> SEQUENCE: 18
cggtcgcaat tgatcattca ctatctctag caggggaaag aacttgggct gaaacaatgg        60
gtgcaaatac cgctgat                                                       77

<210> SEQ ID NO 19

```
<211> LENGTH: 77
<212> TYPE: DNA
<213> ORGANISM: Bacillus anthracis
<220> FEATURE:
<223> OTHER INFORMATION: PA MUTANT: TRP346, MET350 AND LEU352 RESIDUES
      CHANGED TO ALANINE

<400> SEQUENCE: 19
cggtcgcaat tgatcattca ctatctctag caggggaaag aactgcggct gaaacagcgg      60
gtgcaaatac cgctgat                                                    77

<210> SEQ ID NO 20
<211> LENGTH: 36
<212> TYPE: DNA
<213> ORGANISM: Bacillus anthracis
<220> FEATURE:
<223> OTHER INFORMATION: LF MUTANT: TYR148 RESIDUE CHANGED TO ALANINE

<400> SEQUENCE: 20
gtagaaggta ccgaaaaggc actgaacgtt gcttat                               36

<210> SEQ ID NO 21
<211> LENGTH: 39
<212> TYPE: DNA
<213> ORGANISM: Bacillus anthracis
<220> FEATURE:
<223> OTHER INFORMATION: LF MUTANT: TRY149 RESIDUE CHANGED TO ALANINE

<400> SEQUENCE: 21
gtagaaggta ccgaaaaggc actgaacgtt tatgctgaa                            39

<210> SEQ ID NO 22
<211> LENGTH: 42
<212> TYPE: DNA
<213> ORGANISM: Bacillus anthracis
<220> FEATURE:
<223> OTHER INFORMATION: LF MUTANT: ILE151 RESIDUE CHANGED TO ALANINE

<400> SEQUENCE: 22
gtagaaggta ccgaaaaggc actgaacgtt tatgaagcag gt                        42

<210> SEQ ID NO 23
<211> LENGTH: 48
<212> TYPE: DNA
<213> ORGANISM: Bacillus anthracis
<220> FEATURE:
<223> OTHER INFORMATION: LF MUTANT: LYS153 RESIDUE CHANGED TO ALANINE

<400> SEQUENCE: 23
gtagaaggta ccgaaaaggc actgaacgtt tatgaaatag gtgcaata                  48

<210> SEQ ID NO 24
<211> LENGTH: 51
<212> TYPE: DNA
<213> ORGANISM: Bacillus anthracis
<220> FEATURE:
<223> OTHER INFORMATION: LF MUTANT: ASP187 RESIDUE CHANGED TO ALANINE

<400> SEQUENCE: 24
tgtgggatgt tccttaagct gattagtaaa taaaagagct tgttcatctg a              51

<210> SEQ ID NO 25
<211> LENGTH: 42
<212> TYPE: DNA
<213> ORGANISM: Bacillus anthracis
<220> FEATURE:
```

<223> OTHER INFORMATION: LF MUTANT: PHE190 RESIDUE CHANGED TO ALANINE

<400> SEQUENCE: 25
tgtgggatgt tccttaagct gattagtagc taaaagatct tg    42

<210> SEQ ID NO 26
<211> LENGTH: 51
<212> TYPE: DNA
<213> ORGANISM: Bacillus anthracis
<220> FEATURE:
<223> OTHER INFORMATION: LF MUTANT: ASP187, LEU188, LEU189, PHE190
      RESIDUES CHANGED TO ALANINE

<400> SEQUENCE: 26
tgtgggatgt tccttaagct gattagtagc tgcagcagct tgttcatctg a    51

<210> SEQ ID NO 27
<211> LENGTH: 66
<212> TYPE: DNA
<213> ORGANISM: Bacillus anthracis
<220> FEATURE:
<223> OTHER INFORMATION: EF MUTANT: TYR137 RESIDUE CHANGED TO ALANINE

<400> SEQUENCE: 27
ccttacttat gatatcaaga gaaatcccct ttccaatttc agcatatact tctttacttt    60
gttcac    66

<210> SEQ ID NO 28
<211> LENGTH: 66
<212> TYPE: DNA
<213> ORGANISM: Bacillus anthracis
<220> FEATURE:
<223> OTHER INFORMATION: EF MUTANT: TYR138 RESIDUE CHANGED TO ALANINE

<400> SEQUENCE: 28
ccttacttat gatatcaaga gaaatcccct ttccaatttc ataagctact tctttacttt    60
gttcac    66

<210> SEQ ID NO 29
<211> LENGTH: 66
<212> TYPE: DNA
<213> ORGANISM: Bacillus anthracis
<220> FEATURE:
<223> OTHER INFORMATION: EF MUTANT: ILE140 RESIDUE CHANGED TO ALANINE

<400> SEQUENCE: 29
ccttacttat gatatcaaga gaaatcccct ttccagcttc ataatatact tctttacttt    60
gttcac    66

<210> SEQ ID NO 30
<211> LENGTH: 66
<212> TYPE: DNA
<213> ORGANISM: Bacillus anthracis
<220> FEATURE:
<223> OTHER INFORMATION: EF MUTANT: LYS142 RESIDUE CHANGED TO ALANINE

<400> SEQUENCE: 30
ccttacttat gatatcaaga gaaatccccg ctccaatttc ataatatact tctttacttt    60
gttcac    66

PROCESS FOR THE PREPARATION OF NON-TOXIC ANTHRAX VACCINE

FIELD OF THE INVENTION

This invention relates to a Recombinant DNA construct and a process for the preparation of a nontoxic anthrax vaccine.

BACKGROUND OF THE INVENTION

Anthrax, a zoonotic disease is caused by gram-positive, sporulating bacteria, *Bacillus anthracis*. Humans are accidental hosts through food of animal origin, animal products and contamination of the environment with *Bacillus anthracis* (Brachman P. S., 1970, Aninals. N.Y. Acad. Sci. 174, 577-582). Anthrax is one of the oldest known bacterial diseases and occurs in most parts of the world including India. The major virulent factors of *B. anthracis* include poly-D-glutamic acid capsule and a three-component anthrax toxin complex. Anthrax toxin (Leppla S. H., 1991, In Source Book of Bacterial protein toxins, pp 277-302.), comprising of protective antigen PA(83 kDa), lethal factor (LF-(90 kDa) and edema factor (EF-(89 kDa) is a major virulent factor of *B. anthracis*. LF/EF, the catalytic moieties of this complex require PA to enter the cell cytosol. PA in combination with LF (called the lethal toxin), causes death in experimental animals (Smith H. and Keppie J., 1954, Nature, 173, 869-870). PA in combination with EF (called the edema toxin) causes edema in the skin of the experimental animals (Stanley J. L. and Smith H., 1961, J. Gen Microbiol., 26, 49-66). PA is the receptor-binding moiety that facilitates the translocation of the catalytic moieties, LF and EF, into the target cells. After translocation into the cell, LF, a metalloprotease causes cleavage of certain Mitogen so activated protein kinase kinases (MAPKKs) resulting in inactivation of signal transduction pathways (Duesbery N. S., et. al., 1998, Science, 280. 734-737). On the other hand, EF, upon entering the cells, gets activated by calmodulin to cause massive increase in intracellular cAMP levels (Leppla S. H., 1982, Proc. Natl. Acad. Sci. USA., 79, 3162-3166).

The first step of the intoxication process is the binding of PA to the cell surface receptors (Bradley K. A. et al, 2001, Nature, 414, 225-229). After binding to the receptors on the cell surface, PA gets nicked by cell surface proteases to yield a 63-kDa fragment (Klimpel el R. K., et. al., 1992, Proc. Natl. Acad. Sci. USA., 89, 10277-10281) which oligomerizes and binds to LF/EF (Milne J. C., et. al., 1994, J. Biol. Chem., 269, 20607-20612). Binding of LF/EF is competitive. The whole complex then undergoes receptor-mediated endocytosis. Acidification of the endosonie (Friedlander A. M., 1986, J. Biol. Chem.. 261, 7123-7126) results in the insertion of the PA-oligomer into the endosomal membrane to form pores (Milne J. C. and Collier R. J., 1993 Mol. Microbiol., 10, 647-653) through which LF/EF are translocated into the cell cytosol.

PA has four domains that are organized primarily into antiparallel-beta sheets with only a few short helices of less than four turns (Petosa C., et. al., 1997, Nature, 385, 833-838). Domain 1 is responsible for binding to LF/EF during the anthrax intoxication process. Domain 2 is dominated by a beta barrel and plays a role in membrane insertion and translocation. Domain 3 is the smallest domain and is important for oligomerization of PA and possibly also in the binding of PA to LF/EF. Domain 4 is the receptor-binding domain.

Crystal structure of LF, determined recently, shows that LF has 4 domains (Pannifer A. D., et al, 2001, Nature, 414, 229-233). Domain 1 is involved in binding to PA. This domain has significant homology to the N-terminal 1-250 residues of EF. In fact, most of the residues in this region are absolutely conserved.

Of all the three toxin proteins, —PA is the most immunogenic and is an essential component of the vaccine against anthrax (Gladstone G. P., 1946, Br. J. Exp. Pathol, 97, 349-418). It has been observed that the protective efficacy of PA is greatly increased if small quantities of LF or EF are incorporated into the vaccine (Pezard et. al., 1995, infect. Immun., 63, 1369-1372). However, this also happens to be the primary reason of toxigenicity and reactogenicity of the vaccines. Anthrax toxin (Leppla S. H., 1991, In Source Book (of Bacterial protein toxins, pp 277-302.), comprising of protective antigen (PA), lethal factor (LF) and edema factor (EF) is a major virulent factor of *B. anthracis*.

The currently used anthrax vaccine is derived from a non-capsulated, avirulent strain of the bacterium known as Sterne's strain (Sterne M., 1939, J. Vet. Sci. Anim. Ind, 13, 307-312). In Russia and China, the live spore vaccines based on Sterne strain are used. In UK the vaccine is alum precipitated culture filtrate of the Sterne strain while the US vaccine consists of an alhydrogel-adsorbed cell free culture filtrates of a non-capsulating, non proteolytic derived strain V770 isolated from bovine anthrax (Turnbull P. C. B, 1991, Vaccine, 9, 533-539). All these currently used anthrax vaccines, apart from being crude have undefined composition. They are reactogenic and do not provide protection against all natural strains of *B. anthracis*.

U.S. Pat. No. 2,017,606 describes the preparation of anthrax antigen by growing the bacilli with a suitable culture medium, separating the bacilli from the culture medium.

U.S. Pat. No. 2,151,364 describes a method of producing an anthrax vaccine which comprises preparing the suspension of anthrax spores, adding to the suspension a sterile solution containing alum.

RU patent 2,115,433 describes the method of production of anthrax vaccine, which comprises of living spores of non-capsulated strain of *B. anthracis* and protective antigen of *B. anthracis*.

WO patent 000252 describes a method of production of anthrax vaccine using non-toxic protective antigen from *B. anthracis* for use in inducing immune response, which is protective against anthrax.

The drawbacks in the above-mentioned patents are that all of them use *Bacillus anthracis* cultures/spores. *Bacillus anthracis* is an infectious organism and can not be handled without containment facilities. The vaccine prepared is contaminated with other toxic and non-toxic proteins from *Bacillus anthracis* resulting in a number of side effects and reactogenicity.

These vaccines also have a certain degree of residual virulence for certain species of domesticated and laboratory animals. The Sterne strain is toxigenic and is pathogenic at high doses. As a result it is considered unsafe and unsuitable for human use. This vaccine can cause undesirable side effects including necrosis at the site of inoculation.

Therefore there is a need to develop a second-generation anthrax vaccine which does not have side effects and has a well-defined composition.

The object of the present invention is to render the anthrax toxin non-toxic without affecting its immunogenicity, in order to develop a safe and effective anthrax vaccine.

To achieve said object, the present invention provides a recombinant DNA construct comprising an expression vector and a DNA fragment including genes for wild type Protective Antigen (PA) or wild type Lethal Factor (LF) or wild type Edema Factor (EF)

The present invention also provides a recombinant DNA construct comprising:

an expression vector and a DNA fragment including genes for mutant type Protective Antigen (PA) or mutant type Lethal Factor (LF) or mutant type Edema Factor (EF).

Said vector is a prokaryotic vector such as PQE 30 and said expression vector contains T5 promoter and 6X histidine tag.

The DNA fragment is the gene for protective antigen with Alanine-substitution at residue Phe202.

The DNA fragment is the gene for protective antigen with Alanine-substitution at residue Leu203.

The DNA fragment is the gene for protective antigen with Alanine-substitution at residue Pro205.

The said DNA fragment is the gene for protective antigen with Alanine-substitution at residue Ile207.

The DNA fragment is the gene for protective antigen with Alanine-substitution at residues Pro205, Trp226 and Phe236.

The DNA fragment is the gene for protective antigen with Alanine-substitution at residue Phe552.

The DNA fragment is the gene for protective antigen with Alanine-substitution at residue Ile574.

The DNA fragment is the gene for protective antigen with Alanine-substitution at residue Phe552 and Phe554.

The DNA fragment is the gene for protective antigen with Alanine-substitution at residue Ile562 and Ile574.

The DNA fragment is the gene for protective antigen with Alanine-substitution at residue Leu566 and Ile574.

The DNA fragment is the gene for protective antigen ith Alanine-substitution at residue Phe552 and Phe554, Ile562, Leu566 and Ile574.

The DNA fragment is the gene for protective antigen with Alanine-substitution at residue Phe427.

The DNA fragment is the gene for protective antigen with deletion of residue Asp 425.

The DNA fragment is the gene for protective antigen with deletion of residue Phe 427.

The DNA fragment is the gene for protective antigen With Alanine-substitution at residue Trp346.

The DNA fragment is the gene for protective antigen with Alanine-substitution at residue Leu352.

The DNA fragment is the gene for protective antigen with Alanine-substitution at residue Trp346, Met350 and Leu352.

The DNA fragment is the gene for lethal factor with Alanine-substitution at residue Tyr148.

The DNA fragment is the gene for lethal factor with Alanine-substitution at residue Tyr149.

The DNA fragment is the gene for lethal factor with Alanine-substitution at residue Ile151.

The DNA fragment is the gene for lethal factor with Alanine-substitution at residue Lys153.

The DNA fragment is the gene for lethal factor with Alanine-substitution at residue Asp187.

The DNA fragment is the gene for lethal factor with Alanine-substitution at residue Phe190.

The DNA fragment is the gene for lethal factor with Alanine-substitution at residue Asp 187, Leu188, Leu 189 and Phe 190.

The DNA fragment is the gene for edema factor with Alanine-substitution at residue Tyr137.

The DNA fragment is the gene for edema factor with Alanine-substitution at residue Tyr138.

The DNA fragment is the gene for edema factor with Alanine-substitution at residue Ile140.

The DNA fragment is the gene for edema factor with Alanine-substitution at residue Lys142.

The protein encoded by said DNA fragment is expressed in a prokaryotic host. The said prokaryotic host is an E. coli strain.

A protein expressed by gene DNA fragment is wild type PA wild type LF, wild type EF and their mutagenised variants.

This invention further discloses a method for producing mutagenized anthrax toxin protein comprising:

mutagenizing PA LF & EF genes using different mutagenic primers of the kind as herein defined for PCR reaction;

treating said mutant PCR product along with the native template with a n enzyme to cleave the native template of said PCR product;

transforming said mutant product in E. coli strain;

isolating the recombinant construct from transformed E. coli strain and confirming the desired mutation;

transforming the confirmed mutant construct in appropriate E. coli expression strain to express the mutant protein and purifying the said expressed mutant protein.

The purification is carried Out using Ni-NTA chromatography and/or other chromatographic techniques.

The genes are cloned in PQE expression vector containing T5 promoter and 6X histidine tag.

The mutations were affected in the first domain of PA at residues 202, 203, 205. The mutations were affected in the third domain of PA at residues 552, 574 552+554, 562+574, 566+574, 552+554+562+566+574 resulting in mutant proteins that were defective in oligomerization. The mutations were affected in the second domain of PA at residues 425 & 427 of loop 4 of domain 2. These mutations impaired the translocation-ability of PA The mutations were affected in the second domain of PA at residues 346, 352 and 346+350+352 in loop 3 of domain 2 such that PA becomes biologically inactive. The mutations were affected in the $1^{st}$ domain of LF at residues 148, 149, 151, 153, 187, 190 and 187+188+189+ 190 impaired the binding of LF to PA. The mutations were affected in the $1^{st}$ 250 residues of EF.

An anthrax vaccine comprising an anthrax toxin protein is selected from wild type PA or wild type LF or wild type EF.

An anthrax vaccine comprising an anthrax toxin protein selected from mutant type PA or mutant type LF or mutant type EF or a combination thereof.

An anthrax vaccine comprising an anthrax toxin protein selected is a combination of any one selected from wild type PA or wild type LF or wild type EF with any one or more selected from mutant type PA or mutant type LF or mutant type EF.

A pharmaceutical composition comprises an effective amount of an anthrax toxin protein as claimed by the present invention.

BRIEF DESCRIPTION OF THE DRAWINGS:

The present invention will be further explained in detail below with reference to the drawings, wherein FIG. 1 shows cloning of PA, LF and EF in a PQE 30 vector; and FIG. 2 shows site directed mutagenesis using long PCR.

DETAILED DESCRIPTIOON OF THE INVENTION

An ideal vaccine against anthrax should contain PA, LF, EF together, but at the same time it should be non-toxic and safe. Purified recombinant proteins with defined composition may be used in the vaccine to minimize reactogenicity of the vaccine. Further, these anthrax toxin proteins may be rendered non-toxic by introducing mutations that affect the biological activity of the proteins without affecting their structure or immunogenicity. These non-toxic, mutant anthrax toxin proteins may be used together to create a safe, non-reactogenic and effective recombinant vaccine against anthrax. Thus, the prime objective of this invention was to create a process for making a safe and effective, second-generation vaccine against anthrax comprising of non-toxic anthrax toxin proteins that have been produced by site-directed mutagenesis of the different functionally important domains of the toxin proteins.

The inventors of this application have PCR amplified the genes for PA, LF and EF. They have cloned these genes in pQE30 expression vector (Gupta P., et. al., 1998, Infect. Immun., 66, 862-865; Gupta P., et. al., 1999 Protein Expr. Purif. 16, 369-376; Kumar P., et. al. 2001, Infect. Immun., 69, 6532-6536). The vector contains T5 promoter and a 6X -Histidine tag, which allows convenient purification of the recombinant proteins (FIG. 1).

Conditions for overexpression of the said genes using the above mentioned recombinant plasmids, from *E. coli* strains have been optimized by the inventors (Chauhan V., et. al., 2001, Biochem. Biophys. Res. Commun., 283, 308-315).

Using the above mentioned recombinant plasmid, inventors of the present process, introduced mutations in the said genes to make the expressed recombinant proteins defective in their biological function, thereby rendering them non-toxic. The invention involves the expression and purification of the said mutant proteins from *E. coli* strains. It further involves full characterization of the purified mutant proteins to pinpoint the defect that renders them non-toxic.

Mutations Introduced in Protective Antigen as Part of the Invention

1. Mutations that make PA defective in binding to LF/EF. The inventors introduced series of mutations in the $1^{st}$ domain of PA. Among the mutations introduced, the mutations at residues 202, 203, 205, 207 and 205+226+236 were found to be defective in binding to LF.
2. Mutations that make PA defective in oligomerization. The authors of this invention introduced mutations in the $3^{rd}$ domain of PA. The mutation at the residues 552, 574, 552+554, 562+574 566+574, 552+554+562+566+574 resulted in mutant proteins that were defective in oligomerization.
3. Mutations that make PA translocation-defective. Inventors have introduced mutations at residues 425 and 427 of loop 4 of domain 2. These mutations impaired the translocation-ability of PA.
4. Mutations that make PA defective in insertion/translocation. Authors have discovered that when mutations are introduced at the residues 346, 352 and 346+350+352 in loop 3 of domain 2, PA becomes biologically inactive. The mutant proteins were able to bind to the cell-surface receptors, get proteolytically activated to form oligomers and bind to LF. The biological inactivity of these mutant proteins may pertain to a defect in insertion/translocation.

Mutations Introduced in Lethal Factor as Part of the Invention
Mutations that make LF defective in binding to PA. The inventors of this process have introduced mutations in the $1^{st}$ domain of LF. They found that mutation at residues 148, 149, 151, 153, 187, 190 and 187+188+189+190 impaired the binding of LF to PA.

Mutations Introduced in Edema Factor as Part of the Invention
Mutations that make EF defective in binding to PA. The inventors of this process have introduced series of mutations in the $1^{st}$ 250 residues of EF. It was found that mutation at residues 137, 138, 140 and 142 drastically impaired the binding of EF to PA.

After the expression and purification of the mutant proteins the proteins were evaluated for their biological activity.

Inventors have found that the above-mentioned mutants of PA when added along with wild-type LF, were nontoxic to J774A.1 cells. Likewise mutants of LF when added along with wild-type PA were non-toxic to J774A.1 cells. Similarly, mutants of EF when added along with wild-type PA were unable to produce cAMP-toxicity in CHO cells (Table 2).

The purified mutant protein was analyzed for their biological activity by assaying:
   Ability of PA to bind to cell surface receptors,
   Ability of PA to bind to LF or EF,
   Ability of PA to oligomerize,
   Membrane insertion ability of PA oligomer,
   Ability of PA to translocate LF or EF to the cytosol,
   Ability of lethal toxin to kill macrophage cell lines like RAW264.7 and J774A.1
   Ability of edema toxin to elongate CHO cells.

Immunization Studies

Protective antigen, as the name suggests is a highly immunogenic protein. In fact it is a necessary component of the vaccine against anthrax. Immunization with wild-type recombinant PA elicits high anti-PA titers and provides protection against anthrax lethal challenge in guinea pigs. It was further observed that mutant PA was as immunogenic as the wild-type PA and could easily substitute the wild-type PA in vaccine (Singh et. al. 1998, Infect. Immun. 66, 3447-3448). Immunization studies also indicate a significant contribution of LF/EF to immunoprotection. On basis of these results the inventors have developed a recombinant vaccine against anthrax, which comprises mutants of all the three anthrax toxin components.

The anthrax toxin based recombinant vaccine developed by the inventors has the following advantages:
1. The process described here does not involve handling of *B. anthracis* cultures (at any stage). This process is therefore safe, cost-effective and does not require the sophisticated containment facilities.
2. The vaccine developed by the inventors has well-defined composition and will therefore not have any batch to batch variation.
3. The invention described here utilizes purified mutant anthrax toxin protein. As a result, this second-generation anthrax vaccine will not be reactogenic and will not cause any side-effects unlike the previous vaccine.
4. Additionally, this invention comprises of non-toxic mutant proteins, which when administered (either alone or in combination) do not cause any toxigenicity or pathogenicity as associated with the currently used vaccine.
5. The invention described here is therefore safe and suitable for animal/human use.

Details of the Experimental Procedures

Site-directed Mutagenesis of Anthrax Toxin Proteins
To introduce the desired mutations in the anthrax toxin proteins, complementary mutagenic primers were used (refer Table 1) to amplify the wild type anthrax toxin genes (for PA or LF or EF). High fidelity Pfu DNA polymerase was used for the PCR reaction. Entire lengths of both the strands of the plasmid DNA were amplified in a linear fashion during several rounds of thermal cycling, generating a mutant plasmid with staggered nicks on the opposite strands (FIG. 2). The amplification was checked by agarose gel electrophoresis of the PCR product. The product of the amplification was treated with DpnI that specifically cleaves fully methylated $G^{me6}$ATC sequences. The digestion reaction was carried out in 20 µl reaction volume with 10 ng of the amplified product, 2 µl of 10X DpnI reaction buffer and 0.1 U of DpnI. After DpnI digestion, DpnI resistant molecules that are rich in desired mutants were recovered by transformation of the DNA into the appropriate E. coli strain. The mutations were confirmed by sequencing of the above constructs using Perlcin Elmer cycle DNA sequencing kit.

Expression and Purification of the Mutant Anthrax Toxin Proteins

The confined constructs were transformed into E. coli expression strains expressing T5 RNA polymerase. Transformed cells were grown in Luria broth medium (LB) containing 100 µg/ml of ampicillin and 25 µg/ml of kanamycin, at 37° C., to an $OD_{600}$ of 0.8. Induction vas then done with 0.5 mM IPTG and the incubation was continued at 37° C. for 3 to 4 hours. Cells were then harvested by centrifugation at 6000 rpm for 10 minutes. The cells then lysed. The protein profile was analysed by SDS-PAGE and western blotting. The mutant PA proteins were purified using Ni-NTA metal-chelate affinity chromatography and other chromatographic techniques (Kumar P., et. al. 2001, Infect. Immun., 69, 6532-6536; Gupta P., et. al., 1998, Infect. Immun., 66, 862-865; Gupta P., et. al., 1999 Protein Expr. Purif. 16, 369-376). The purified mutant proteins were analysed by SDS-PAGE and western blotting and were estimated using Bradford's method. For storage the purified proteins were dialysed against 50 mM HEPES and stored as aliquotes at −70° C.

Cell Culture

Macrophage like cell line J774A.1 was maintained in RPMI 1640 medium containing 10% heat inactivated FCS, 25 mM HEPES, 100U/ml penicillin and 200 µg/ml streptomycin in a humidified 5% $CO_2$ environment at 37° C.

CHO cells were maintained in EMEM medium containing 10% heat inactivated FCS, 25 mM HEPES, 100U/ml penicillin and 200 µg/ml streptomycin in a humidified 5% $CO_2$ environment at 37° C.

To study the biological activity of the wild-type PA or its mutant proteins, varying concentrations of these proteins were added along with LF (1 µg/ml) to J774A.1 cells plated in 96-wells plates. Incubation was allowed for 3 hrs. at 37° C. and then cell viability (Bhatnagar et. al. 1989, Infect. Immun., 57, 2107-2114) was determined using 3-(4,5-dimethylthiazol-2-yl)-2,5-diphenyltetrazoliumbromide (MTT) dye (Bhatnagar R., et. al., 1999, Cell Signal., 11, 111-116). MT-T dissolved in RPMI was added to each well at a final concentration of 0.5 mg/ml and incubated for another 45 min at 37° C. to allow uptake and oxidation of the dye by viable cells. The medium was replaced by 0.5% (w/v) sodium dodecyl sulphate (SDS), 25 mM HCl in 90% isopropyl alcohol and the plate vortexed. The absorption was read at 540 nm using microplate reader (BIORAD).

Similarly, to study the biological activity of wild-type LF or its mutant proteins, varying concentrations of these proteins were added along with PA (1 µg/ml) to J774A.1 cells plated in 96-wells plates. Incubation was allowed for 3 hrs. at 37° C. and then cell viability as determined using MTT dye, as detailed above.

To study the biological activity of wild-type EF or its mutant proteins, varying concentrations of these proteins were added along with PA (1 µg/ml) to CHO cells that were plated in 96-wells plates. Incubation was allowed for 3 hrs. at 37° C. and then the cells were microscopically examined for elongation. Rise in intracellular cAMP levels of the cells upon toxin treatment was determined (Kumar P., et. al., 2001, Infect. Immun., 69, 6532-6536) with cAMP EIA kit of Amersham Pharmacia.

Further experiments were then done to understand how mutations were affecting the biological activity of the anthrax toxin mutant proteins.

Binding of PA to Cell Surface Receptors

J774A.1 cells were allowed to grow to confluence in 24-well plates before incubating with 1 µg/ml of wild-type PA or its mutant protein at 4° C. for 2 hrs. The cells were then washed with cold RPMI, dissolved in SDS lysis buffer and subjected to SDS-PAGE for electroblotting. The blot was developed with anti-PA antibodies to study the binding of wild-type PA or its mutant protein with the cell surface receptors Proteolytic Cleavage of PA and Mutant Proteins in Solution Wild-type PA and its mutant proteins were tested for susceptibility to cleavage by trypsin. The proteins (1.0 mg/ml) were incubated with 1 µg/ml of trypsin for 30 minutes at room temperature in 25 mM HEPES, 1 mM $CaCl_2$, 0.5 mM EDTA pH 7.5. The digestion reaction was stopped by adding PMSF to a concentration of 1 mM. For SDS-PAGE, the samples were boiled in SDS sample buffer for 5 minutes and resolved on 12% SDS-PAGE.

Binding of PA to LF on the Surface of Cells

J774A. 1 cells were washed twice with RPMI and then incubated with 1 µg/ml of wild-type PA or its mutant protein at 4° C. for 3 hrs. The cells were then washed with cold RPMI to remove unbound protein. The cells were further incubated with LF (1.0 µg/ml) for 3 hours and then washed with cold RPMI to remove unbound LF. The cells were dissolved in SDS lysis buffer and subjected to SDS-PAGE for electroblotting. The blot was developed with anti-LF antibodies to study the binding of the wild-type PA or its mutant protein to LF.

Oligomerization of PA in Solution

PA upon proteolytic cleavage oligomerises to form heptamers. To study the ability of the wild-type PA and its mutant proteins to form oligomers, the proteins (1 mg/ml) were digested with trypsin for 30 minutes at 25° C. The samples were brought to pH 5.0 by addition of 1M Tris pH5.0 to a final concentration of 100 mM. and were boiled for 5 minutes in SDS sample buffer (0.0625M Tris-Cl, 1.25% SDS, 2.5%, β-mercaptoethanol and 5% glycerol, pH6.8) before loading on a 3-12% gradient gel. Silver staining was done to detect the formation of oligomers.

Binding of LF/EF to Cell-surface Bound PA.

J774A.1 cells were washed with cold RPMI and then incubated with 1 µg/ml of wild-type PA at 4° C. for 3 hrs. The cells were washed again with cold RPMI to remove unbound protein. Wild-type LF/EF or the mutant proteins (1.0 µg/ml) were then added and incubation was continued for 3 hours. The cells were then washed with cold RPMI to remove unbound LF/EF. Later, the cells were dissolved in SDS lysis buffer and subjected to SDS-PAGE for electroblotting. The blot was developed with anti-LF/EF antibodies to study the binding of LF/EF to cell-surface bound.

| RESIDUE | CHANGE | PRIMERS | DOMAIN | DEFECT |
|---|---|---|---|---|
| PA mutants: | | | | |
| Phe202 | To alanine | 5'CTTTTCATGAATATTAGAAATCCATGCTGAAAG (SEQ ID NO: 1) | I | Defective in binding to Lethal factor |
| Leu203 | To alanine | CTTTTCATGAATATTAGAAATCCATGGTGAAGCAAAAGT (SEQ ID NO: 2) | I | Defective in binding to Lethal factor |
| Pro205 | To alanine | CTTTTCATGAATATTAGAAATCCATGGTGAAAGAGCAGTTCT (SEQ ID NO: 3) | I | Defective in binding to Lethal factor |
| Ile207 | To alanine | TTTGGTTAACCCTTTCTTTTCATGAATATTAGAAATCCATGGT GAAAGAAAAGTTCTTTTATTTTTGACATCAACCGTATATCCTT CTACCTCTAATGAATCAGCGATTCC (SEQ ID NO: 4) | I | Defective in binding to Lethal factor |
| Pro205 + Trp226 + Phe236 | To alanine | CTTTTCATGAATATTAGAAATCCATGGTGAAAGAGCAGTTCT (SEQ ID NO: 5) and GGATTTCTAATATTCATGAAAGAAAGGATTAACCAAATATA AATCATCTCCTGAAAAAGCGAGCACGGCTTCTGATCCGTACA GTGATGCCGAAAAGGTT (SEQ ID NO: 6) | I | Defective in binding to Lethal factor |
| Phe552 | To alanine | CAAGGGAAAGATATCACCGAATTTGATGCTAATTTCGATC (SEQ ID NO: 7) | III | Oligomerization defective |
| Ile574 | To alanine | GAATTAAACGCGTCTAACGCATATACTG (SEQ ID NO: 8) | III | Oligomerization defective |
| Phe552 + Phe554 | To alanine | ATTTTGAGATGTTTGTTGATCGGCATTAGCATCAAATTC (SEQ ID NO: 9) | III | Oligomerization defective |
| Ile562 + Ile574 | To alanine | CAGTATATGCGTTAGACGCGTTTAATTCCGCTTAACTGATTCT TGGCATTTTGAGATG (SEQ ID NO: 10) | III | Oligomerization defective |
| Leu566 + Ile574 | To alanine | ATCAGGCAGCGGAATTAAACGCGTCTAACGCATATACTG (SEQ ID NO: 11) | III | Oligomerization defective |
| Phe552 + Phe554 + Ile562 + Leu566 + Ile574 | To alanine | CAGTATATGCGTTAGACGCGTTTAATTCCGCTGCCTGATTCTT GGCATTTTGAGATG (SEQ ID NO: 12) and ATTTTGAGATGTTTGTTGATCGGCATTAGCATCAAATT (SEQ ID NO: 13) | III | Oligomerization defective |
| Phe427 | To alanine | GTAATTGGAGTAGAACTGGCATCGTCTTGTGC (SEQ ID NO: 14) | II | Translocation defective |
| Asp425 | Residue deleted | GTAATTGGAGTAGAACTGAAATCTTGTTCATTTAATGCG (SEQ ID NO: 15) | II | Translocation defective |
| Phe427 | Residue deleted | GCACAAGACGATAGTTCTACTCCAATTAC (SEQ ID NO: 16) | II | Translocation defective |
| Trp346 | To alanine | CGGTCGCAATTGATCATTCACTATCTCTAGCAGGGGAAAGAA CTGCGGCTGAAACAATG (SEQ ID NO: 17) | II | Membrane insertion/ translocation defective |
| Leu352 | To alanine | CGGTCGCAATTGATCATTCACTATCTCTAGCAGGGGAAAGAA CTTGGGCTGAAACAATGGGTGCAAATACCGCTGAT (SEQ ID NO: 18) | II | Membrane insertion/ translocation defective |
| Trp346, Met350 and Leu352 | To alanine | CGGTCGCAATTGATCATTCACTATCTCTAGCAGGGGAAAGAA CTGCGGCTGAAACAGCGGGTGCAAATACCGCTGAT (SEQ ID NO: 19) | II | Membrane insertion/ translocation defective |
| LF mutants: | | | | |
| Tyr148 | To alanine | GTAGAAGGTACCGAAAAGGCACTGAACGTTGCTTAT (SEQ ID NO: 20) | I | Defective in binding to Protective Antigen |
| Tyr149 | To alanine | GTAGAAGGTACCGAAAAGGCACTGAACGTTTATGCTGAA (SEQ ID NO: 21) | I | Defective in binding to Protective Antigen |

-continued

| RESIDUE | CHANGE | PRIMERS | DOMAIN | DEFECT |
|---|---|---|---|---|
| Ile151 | To alanine | GTAGAAGGTACCGAAAAGGCACTGAACGTTTATGAAGCAGGT (SEQ ID NO: 22) | I | Defective in binding to Protective Antigen |
| Lys153 | To alanine | GTAGAAGGTACCGAAAAGGCACTGAACGTTTATGAAATAGGT GCAATA (SEQ ID NO: 23) | I | Defective in binding to Protective Antigen |
| Asp187 | To alanine | TGTGGGATGTTCCTTAAGCTGATTAGTAAATAAAAGAGCTTGT TCATCTGA (SEQ ID NO: 24) | I | Defective in binding to Protective Antigen |
| Phe190 | To alanine | TGTGGGATGTTCCTTAAGCTGATTAGTAGCTAAAAGATCTTG (SEQ ID NO: 25) | I | Defective in binding to Protective Antigen |
| Asp187, Leu188, Leu189, Phe190 | To alanine | TGTGGGATGTTCCTTAAGCTGATTAGTAGCTGGAGCAGCTTGT TCATCTGA (SEQ ID NO: 26) | I | Defective in binding to Protective Antigen |
| EF mutants: | | | | |
| Tyr137 | To alanine | CCTTACTTATGATATCAAGAGAAATCCCC TTT CC AAT TTC AGC ATA TAC TTC TTT ACT TTG TTC AC (SEQ ID NO: 27) | | Defective in binding to Protective Antigen |
| Tyr138 | To alanine | CCTTACTTATGATATCAAGAGAAATCCCC TTT CC AAT TTC ATA AGCTAC TTC TTT ACT TTG TTC AC (SEQ ID NO: 28) | | Defective in binding to Protective Antigen |
| Ile140 | To alanine | CCTTACTTATGATATCAAGAGAAATCCCC TTT CCAGCTTC ATA ATATAC TTC TTT ACT TTG TTC AC (SEQ ID NO: 29) | | Defective in binding to Protective Antigen |
| Lys142 | To alanine | CCTTACTTATGATATCAAGAGAAATCCCC GCT CC AAT TTC ATA ATATAC TTC TTT ACT TTG TTC AC (SEQ ID NO: 30) | | Defective in binding to Protective Antigen |

TABLE 2

CHARACTERISTICS OF MUTANTS

| MUTATION IN PA | RECEPTOR BINDING | TRYPSIN NICKING | OLIGOMER FORMATION | LF/EF BINDING | TOXICITY |
|---|---|---|---|---|---|
| Phe202Ala | + | + | + | − | − |
| Leu203Ala | + | + | + | − | − |
| Pro205Ala | + | + | + | − | − |
| Ile207Ala | + | + | + | − | − |
| Pro205Ala + Trp226Ala + Phe236Ala | + | + | + | − | − |
| Phe552Ala | + | + | − | − | − |
| Ile574Ala | + | + | − | − | − |
| Phe552Ala + Phe554Ala | + | + | − | − | − |
| Ile562Ala + Ile574Ala | + | + | − | − | − |
| Leu566Ala + Ile574Ala | + | + | − | − | − |
| Phe552Ala + Phe554Ala + Ile562Ala + Leu566ala + Ile574Ala | + | + | − | − | − |
| Phe427Ala | + | + | + | + | − |
| Asp425del | + | + | + | + | − |
| Phe427del | + | + | + | + | − |
| Trp346Ala | + | + | + | + | − |
| Leu352Ala | + | + | + | + | − |
| Trp346Ala + | + | + | + | + | − |

TABLE 2-continued

CHARACTERISTICS OF MUTANTS

Met350Ala + Leu352Ala

| MUTATION IN LF | BINDING TO PA | TOXICITY |
|---|---|---|
| Tyr148Ala | − | − |
| Tyr149Ala | − | − |
| Ile151Ala | − | − |
| Lys153Ala | − | − |
| Asp187Ala | − | − |
| Phe190Ala | − | − |
| Asp187Ala + Leu188Ala + Phe190Leu189Ala | − | − |

| MUTATION IN EF | BINDING TO PA | TOXICITY |
|---|---|---|
| Tyr137Ala | − | − |
| Tyr138Ala | − | − |
| Ile140Ala | − | − |
| Lys142Ala | − | − |

We claim:

1. A recombinant DNA construct for expressing mutagenized toxin protein of *Bacillus anthracis* comprising:
   A) an expression vector, and
   B) a DNA fragment comprising a gene encoding mutant type Protective Antigen (PA), mutant type Lethal Factor (LF) or mutant type Edema Factor (EF), or a combination thereof wherein the DNA fragment comprises a non-native sequence that results from amplifying at least one of (i) a gene encoding native Protective Antigen (PA) with a primer selected from the group consisting of SEQ ID NO: 1, 2, 3, 4, 5, and 6; (ii) amplifying a gene encoding native Lethal Factor (LF) with a primer selected from the group consisting of SEQ ID NO: 20, 21, 22, 23, 24, 25 and 26; and (iii) amplifying a gene encoding native Edema Factor (EF) with a primer selected from the group consisting of SEQ ID NO: 27, 28, 29 and 30.

2. A recombinant DNA construct as claimed in claim 1, wherein said expression vector is a prokaryotic vector.

3. A recombinant DNA construct as claimed in claim 2, wherein said prokaryotic expression vector is pQE30.

4. A recombinant DNA construct as claimed in claim 3, wherein said prokaryotic expression vector contains T5 promoter and 6X histidine tag.

5. A mutagenized PA, LF or EF anthrax toxin protein of *Bacillus anthracis*, expressed by the recombinant DNA construct of claim 1, wherein the protein possesses immunogenic properties.

6. A method of producing a mutagenized PA, LF or EF anthrax toxin protein, wherein the method comprises the following steps:
   a) producing a mutant gene encoding a mutant toxin protein PA, LF or EF by amplifying a native PA, LF or EF template in a polymerase chain reaction using a primer selected from the group consisting of SEQ ID NO: 1, 2, 3, 4, 5, 6, 20, 21, 22, 23, 24, 25, 26, 27, 28, 29 and 30 to form mutant polymerase chain reaction products,
   b) treating the mutant polymerase chain reaction products along with the native template from step a) with an enzyme to cleave the native template of said polymerase chain reaction products to form mutant products,
   c) transforming a prokaryotic host with said mutant products of step b to cause the prokaryotic host to express the mutagenized PA, LF or EF anthrax toxin protein, and
   d) purifying the expressed mutagenized PA, LF or EF anthrax toxin protein.

7. A method as claimed in claim 6, wherein the prokaryotic host is an *E. coli* strain.

8. A method as claimed in claim 6, wherein said enzyme is DpnI enzyme that specifically cleaves fully methylated target sequence $G^{me6}$ ATC.

9. A method as claimed in claim 6, wherein saidm—mutant gene is cloned in a pQE30 expression vector under the control of T5 promoter and 6X histidine tag fusion.

10. A method as claimed in claim 6, wherein said purification is carried out using Ni-NTA affinity chromatography.

11. An anthrax vaccine comprising a mutant toxin protein of *Bacillus anthracis* encoded by the recombinant DNA construct of claim 1, said vaccine comprising a mutant toxin protein PA, LF or EF, or a combination thereof.

12. An anthrax vaccine comprising one or more mutagenized anthrax toxin proteins of claim 5, in combination with a toxin protein of *Bacillus anthracis* of wild-type PA or wild-type LF or wild-type EF.

13. A mutagenized PA anthrax toxin protein produced by the method of claim 6.

14. A mutagenized LF anthrax toxin protein produced by the method of claim 6.

15. A mutagenized EF anthrax toxin protein produced by the method of claim 6.

16. A recombinant DNA construct as claimed in claim 1, wherein the DNA fragment comprises a non-native sequence that results from amplifying a gene encoding native Protective Antigen (PA).

17. A recombinant DNA construct as claimed in claim 1, wherein the DNA fragment comprises a non-native sequence that results from amplifying a gene encoding native Lethal Factor (LF).

18. A recombinant DNA construct as claimed in claim 1, wherein the DNA fragment comprises a non-native sequence that results from amplifying a gene encoding native Edema Factor (EF).

* * * * *